United States Patent
Cotrell et al.

(10) Patent No.: US 6,566,408 B1
(45) Date of Patent: May 20, 2003

(54) AQUEOUS SURFACTANT COMPOSITIONS OF MONOALKYL PHOSPHATE ESTER SALTS AND AMPHOTERIC SURFACTANTS

(75) Inventors: Phillip Loraine Cotrell, New Egypt, NJ (US); Alvino Gabbianelli, Fairless Hills, PA (US); Robert Lee Reierson, Princeton Jct., NJ (US)

(73) Assignee: Rhodia, Inc., Cranbury, NJ (US)

( * ) Notice: Subject to any disclaimer, the term of this patent is extended or adjusted under 35 U.S.C. 154(b) by 0 days.

(21) Appl. No.: 09/630,068

(22) Filed: Aug. 1, 2000

(51) Int. Cl.[7] .......................... B01F 17/14; B01F 17/24; A61K 7/975; A61K 7/08
(52) U.S. Cl. .................. 516/56; 424/70.19; 424/70.21; 424/70.23; 510/122; 510/159; 510/436; 510/501; 516/13; 516/907; 516/908
(58) Field of Search ..................... 516/13, 56, 907, 516/908; 510/122, 436, 159, 501; 424/70.23, 70.19, 70.21

(56) References Cited

U.S. PATENT DOCUMENTS

| | | | | |
|---|---|---|---|---|
| 4,049,556 A | * | 9/1977 | Tujimoto et al. | ......... 516/56 X |
| 4,139,485 A | | 2/1979 | Imokawa et al. | |
| 4,758,376 A | * | 7/1988 | Hirota et al. | ........... 510/122 X |
| 5,139,781 A | * | 8/1992 | Birtwistle et al. | ........ 516/13 X |
| 5,334,387 A | * | 8/1994 | Haugk | ............... 510/122 X |
| 5,463,101 A | | 10/1995 | Reierson | ..................... 558/110 |
| 5,550,274 A | | 8/1996 | Reierson | ..................... 558/110 |
| 5,554,781 A | | 9/1996 | Reierson | ..................... 558/110 |
| 5,686,403 A | * | 11/1997 | Matsumoto et al. | .... 510/159 X |
| 5,711,899 A | * | 1/1998 | Kawa et al. | ......... 424/70.19 X |
| 5,744,063 A | * | 4/1998 | Desai et al. | ............ 510/500 X |
| 6,262,130 B1 | * | 7/2001 | Derian et al. | .................. 516/56 |

FOREIGN PATENT DOCUMENTS

EP    675 076 A2    10/1995    ........... C01B/25/24

* cited by examiner

Primary Examiner—Richard D. Lovering
(74) Attorney, Agent, or Firm—Ohlandt, Greeley, Ruggiero & Perle, L.L.P.

(57) ABSTRACT

Aqueous surfactant compositions of alkyl phosphate ester salts having a molar ratio of mono- to di-alkyl phosphate esters equal to or greater than 80:20, and amphoteric surfactants essentially free of tetra-alkyl ammonium moieties. The aqueous surfactant compositions have very low dermal irritation properties.

15 Claims, 5 Drawing Sheets

AQUEOUS SURFACTANT COMPOSITIONS OF MONOALKYL PHOSPHATE ESTER SALTS AND AMPHOTERIC SURFACTANTS

FIELD OF THE INVENTION

This invention relates to novel aqueous surfactant compositions, particularly to surfactant compositions of alkyl phosphate ester salts and amphoteric surfactants. More particularly, this invention relates to essentially non-irritating aqueous surfactant compositions containing alkyl phosphate ester salts having a high monoalkyl phosphate content and amphoteric surfactants.

BACKGROUND OF THE INVENTION

A wide variety of surfactants and mixtures of surfactants are known for many industrial, commercial and domestic applications. In these uses, there is often a need for the surfactant to be in a pumpable or fluid form for addition to formulations requiring the surfactant since such form enables one to save costs in handling and storing of the composition, as well as ease and convenience in formulating products therewith. Additionally, for numerous reasons, such as formulation flexibility, transportation and storage costs, it is desirable for the surfactant to be available in such pumpable compositions in as high a concentration or proportion of surfactant or active ingredient as possible.

The superior performance of fatty alcohol-based anionic phosphate esters of high monoalkyl phosphate ester content relative to dialkyl phosphate ester content, especially at a ratio of at least 80:20 or more, has long been recognized, especially for their mildness, detergency and foaming properties, and particularly for use in cosmetic or personal care products like shampoos, conditioners and body cleansers. See U.S. Pat. No. 4,139,485 to G. Imokawa et al., issued Feb. 13, 1979. Their usefulness in the latter products is due, at least in part, to their ability to produce high detergency with low skin irritancy compared to other surfactants, such as alkyl sulphates, alkyl ether sulphates, polyoxyethylene alkyl sulphates, alkyl benzene sulphonates and the like. Moreover, such fatty alcohol-based anionic phosphate ester surfactants of high monoalkyl ester content provide surfactants that evidence an excellent balance of properties. For example, as the monoalkyl phosphate content increases relative to the dialkyl phosphate content, the solubility, foaming ability and detergency increase. Additionally, the increase in monoalkyl phosphate content reduces the skin irritancy effect.

BRIEF SUMMARY OF THE INVENTION

The novel aqueous surfactant compositions of this invention consist essentially of alkyl phosphate ester salts high in monoalkyl phosphate content and an amphoteric surfactant, wherein said composition is essentially free of compounds having a tetra-alkyl ammonium moiety. This invention also provides aqueous compositions which are comprised of an alkyl phosphate ester salt surfactant composition in which the monoalkyl phosphate (1) and dialkyl phosphate (2) are present in a molar ratio of equal to or greater than 50:50, and an amphoteric surfactant. The amphoteric surfactants useful in this invention do not contain a tetra-alkyl ammonium moiety.

"Alkyl phosphate ester salts" is meant to include alkylether phosphate ester salts (i.e. polyoxyalkylene derivatives of the alkanol(s) from which they are derived) as well as non-alkoxylated derivatives. Preferred alkyl phosphate ester salts are mixtures of compounds having the formula (1) and (2):

wherein $R_1$ and $R_2$ are individually $C_8$–$C_{22}$ linear or branched saturated or unsaturated hydrocarbons, m and n are individually integers from 2 to 4, w, x, y and z are individually integers from 0 to 20 and M is individually hydrogen, an alkali metal, amine or alkanolamine.

BRIEF DESCRIPTION OF THE DRAWINGS

The invention is illustrated, but not limited, by the attached drawings in which.

DETAILED DESCRIPTION AND PREFERRED EMBODIMENTS

The compositions are especially useful in cosmetic and personal care products because of the non-irritating-properties of the blend. The aqueous surfactant compositions are preferably essentially free of betaine -surfactants, sultaine surfactants, cocoamphodiacetates and cocoamphodipropionates.

This description will now turn to the individual components of the compositions of this invention. One of the components is an alkyl phosphate ester that is preferably in the form of a high solids, yet pumpable aqueous composition.

Pumpable aqueous surfactant compositions which are particularly useful in this invention are characterized by a low level of residual phosphoric acid and residual alcohol. Pumpable aqueous surfactant compositions of this invention are produced from alkyl phosphate ester compositions high in monoalkyl phosphates relative to dialkyl phosphates, i.e., a molar ratio of mono- to di-alkyl phosphate esters of equal to or greater than 50:50, preferably 80:20 or greater and more preferably greater than 90:10. The phosphate ester compositions of low residual phosphoric acid and residual alcohol content and high in monoalkyl phosphates used to produce the aqueous pumpable surfactant composition of this invention are produced by the process disclosed in U.S.

Pat. Nos. 5,463,101, 5,550,274 and 5,554,781, as well as in EP Patent publication number EP 0 675,076 A2, especially as described in Example 18 of the EP publication.

The alkyl phosphate ester salts are prepared by stirring the appropriate alkyl phosphate esters, high in monoalkyl phosphate ester content, into a solution of an appropriate base. As examples of suitable base materials for producing the salts of the alkyl phosphate esters, there may be mentioned sodium, potassium, lithium, or ammonium hydroxides and amines, such as for example, triethanolamine (TEA) and 2-amino-2-methyl-1-propanol (AMP) and the like. The salts of the monoalkyl phosphate esters may be of any suitable base:acid molar ratio salts, such as 0.8, 1, 1.5, 1.7 salts and the like.

Alkyl phosphate esters employed in forming the pumpable aqueous surfactant compositions of this invention are preferably produced from alcohols or mixtures of alcohols typically found in natural oils, for example, coconut oils or rapeseed, carbon chain length of about $C_8$ to $C_{22}$, and/or their alkylene oxide derivatives prepared by reaction with ethylene oxide, propylene oxide or both, randomly or in blocked segments. Blends of linear and branched, saturated and unsaturated alcohols and their alkoxylates are permissable but at least about 50% by weight, more preferably at least about 70% by weight, and most preferably, at least about 90% by weight, of the blend should be alcohols having 12 or fewer carbon atom chains. These alcohols are employed in the phosphation processes described in the aforementioned three U.S. Patents and the EP Patent publication. As examples of such alcohol starting materials, there may be mentioned octanol, decanol, dodecanol, tetradecanol, hexadecanol, octadecanol, eicosanol and docosanol or mixtures of alcohols, such as a commercially available blend of a mixture of about 0.1% decanol, about 68.3% dodecanol, about 27.6% tetradecanol and about 4.9% hexadecanol. Preferably, the alkyl phosphate ester salts comprise salts of predominately $C_{10}$ to $C_{12}$ alcohols or $C_8$ to $C_{16}$ alcohols.

Pumpable aqueous surfactant compositions of this invention have a mono- to di-alkyl phosphate molar ratio of at least 50:50 but preferably equal to or greater than 80:20 for applications requiring greater foaming and detergency and have a solids content of about 20% by weight or more and exhibit one or more pumpable regions over a range of pH values for the aqueous surfactant composition, especially over the pH range of from about pH 5 to about pH 10. The pumpable compositions could be, for example, in a lamellar or micellar phase.

The residual phosphoric acid or residual alcohol content of the pumpable aqueous surfactant compositions of this invention will generally be less than 8% by weight, preferably less than 6% by weight, and more preferably less than 5% by weight of each residual component. Higher phosphoric acid content contributes to higher viscosity and salt content and the alcohols, having lower solubility in water, tend to separate or contribute haze to the solution.

Especially preferred are those pumpable aqueous surfactant compositions of this invention which are essentially transparent, more particularly are essentially clear, and even more preferably are essentially colorless when in their pumpable regions.

Pumpable aqueous surfactant compositions of this invention are characterized by being pumpable or flowable at low temperatures, for example, at temperatures of below 40° C., especially in the range of temperatures of from about 5° C. to about 40° C.

While the total solids content of the pumpable aqueous surfactant composition is at least about 20% by weight, it will generally be from about 40% to about 70% by weight alkyl phosphate ester salt.

The amphoteric surfactants useful in the present invention include the imidazoline-based and fatty amine-based surfactants. Examples include the imidazoline based amphoteric surfactants such as cocoamidoalkylamino monoacetate (available from Rhodia Inc., as Miranol Ultra C-37) and cocoamidoalkylamino monopropionate (available from Rhodia Inc., as Miranol Ultra CM-SF), sodium cocoamidoalkylamino hydroxypropyl sulfonate (available from Rhodia Inc., as Miranol CS), and sodium caprylamidoalkylamino hydroxypropyl sulfonate (available from Rhodia Inc., as Miranol JS), and the fatty alkyl amine-based amphoteric surfactants such as cocoalkylamine acetates, cocoalkylamine diacetates, cocoalkylamine propionates, cocoalkylamine dipropionates, and cocoalkylamine hydroxypropylsulfonates.

Preferred amphoteric surfactants are the those described in U.S. Pat. No. 5,744,063, the disclosure of which is incorporated herein by reference. Those surfactants are imidazoline-based amphoteric surfactants of high purity and which contain essentially negligible amounts of unalkylated amidoamines, lower amounts of glycolic acid salts, and monchloroacetate salts.

The compositions of the present invention are made by blending alkyl phosphate ester salts high in monoalkyl phosphate content and amphoteric surfactants. The blends will typically have a total solids content of from about 5% to about 40% with a ratio of active phosphate ester surfactant to active amphoteric surfactant of from about 100:1 to about 1:100, more typically from about 10:1 to about 1:10, and even more typically from about 3:1 to about 1:3.

The invention is illustrated by the following illustrative, but non-limiting, examples. All phosphate esters were prepared by phosphation of the selected alcohol or blend of alcohols in accordance with the processes described in European Patent publication EP 0 675,076 A2, particularly Example 18 thereof, with adjustment of reagent charges as appropriate for different alcohol molecular weights or intended ester product distributions.

EXAMPLES

Preparation of Monoalkyl Phosphates

Example 1

Preparation of Dodecyl Phosphate

A pre-dried reactor was charged, under essentially anhydrous conditions of a dry nitrogen blanket, with 343.5 lb. dodecanol which was heated to 35° C. to melt and provide an easily stirrable liquid. Polyphosphoric acid, (115%), 111.3 lb., was then added to the stirred liquor with cooling to maintain the temperature below 45° C. Stirring was continued for 30 min. to assure a homogenous solution. Phosphoric anhydride powder, 40.0 lb., was then added with cooling to maintain the temperature under 55° C. and the rapidly stirred mixture was heated to 80° C. and held at that temperature. Reaction progress was followed by the change in the second acid value and, after it had stabilized, 2.5 lb. water was added and stirring was continued at 80° C. for two hours. The batch was then cooled to 65° C., 1.0 lb. 35% hydrogen peroxide was added, the solution stirred for 30 minutes and readied for transfer. The product composition, determined by $^{31}$P, $^{13}$C and $^1$H nuclear magnetic resonance spectroscopy, was, by weight, 6.2% phosphoric acid, 76.0% mono(dodecyl) phosphate, 12.4% di(dodecyl) phosphate, 4.8% nonionics (residual alcohol) and 0.6% water (Karl-Fischer titration). Acid value 1 (first titration inflection point, pH~5.6) was 210.7 mg KOH/g sample.

Example 2

Preparation of Aqueous, 42% Potassium Dodecyl Phosphate Solution

To a clean, dry reactor was sequentially charged 235.2 lb. potassium hydroxide solution (45%) and 397.5 lb. deionized water. The solution was heated to 60° C., which is above the melting point of the acid phosphate ester, and a 351.7 lb. portion of the molten product mixture from the above Example 1 was pumped into the stirred liquor with cooling to maintain the temperature at 60°–65° C. Stirring was continued for an hour to assure a uniform solution, the batch was cooled to below 50° C. and transferred to storage. The % solids determined on a Mettler LJ16 moisture analyzer (120° C., 120 min.) was 42 wt. % and the Karl-Fisher titration moisture was 58 wt. %. The pH of the clear, colorless solution was 8.20 and viscosity (@25° C.) was 50 cps. The theoretical % solids was calculated to be 43% and potassium/phosphorus (K/P) molar ratio, 1.43. This material was used as the "MAP" and "K-MAP" listed in the Summary Table and the Figures.

Amphoteric Surfactants

The "Amphoteric" surfactant used in the following study and shown in the "Summary Table" was from Rhodia Inc., Miranol Ultra C-37, lot #DA7G008686, 37.3% active, color 1.5 (Gardner), 44.2% solids, chloride (as NaCl)=6.91%, viscosity @ 25C with #2 spindle rotating @ 12 RPM =190 CPS, pH @ 25C=9.42.

In the following study, the tested solutions were at a total surfactant actives content of 0.5% by weight. (The surfactant actives of the solution of Example 2, above, was taken to be 42%.) The ratio shown in the Summary Table below is the weight ratio of surfactant actives to surfactant actives.

Summary Table

| Article No. | Surfactant | Ratio or Concentration | pH |
|---|---|---|---|
| 1 | MAP/Ultra C-37 | 1:0.5 | 5.97 |
| 2 | MAP/Ultra C-37 | 1.1 | 6.03 |
| 5 | MAP/SLES-2 Ultra C-37 | 0.5:0.5:0.5 | 5.97 |
| 3 | MAP/Betaine | 1:0.5 | 6.05 |
| 8 | UM-140 | 0.5 | 6.02 |
| 6 | MAP/SLES-2 Ultra C-3 | 0.5:0.5:1 | 6.02 |
| 7 | UM-140 | 0.5 | 5.99 |
| 4 | MAP/Betaine | 1:1 | 6.07 |
| 9 | SLS | 0.5 | — |

SLES-2 = sodium lauryl ether sulphate (2 mol EO)
Betaine = cocoamidopropyl betaine (Bet C-30)
UM-140 = mixture of sodium cocoyl isethionate, sodium, lauroamphoacetate and sodium methyl cocyl taurate surfactants.
SLS = Sodium lauryl sulphate @ 0.5% aqueous.

The improved reduction in dermal irritation properties of the aqueous surfactant compositions of this invention is illustrated by the results in the following tests.

14-Day Cumulative Irritation Assay of the Comparitive Dermal Irritation Potential of a Series of Test Articles The objective of this study was to determine the comparative dermal irritation potential of a series of nine (9) test articles on twenty-five (25) subjects using a 14-Day Cumulative Irritation Assay.

Study Population

Twenty-five (25) subjects, 1 male and 24 females, ranging in age from 18 to 55 years were empaneled for this test.

The subjects chosen were dependable and able to read and understand instructions. The subjects did not exhibit any physical or dermatological condition that would have precluded application of the test articles.

Study Design

A sufficient amount of each test article (approximately 0.2 ml) was placed onto a Parke-Davis Readi-Bandage® occlusive patch, which was applied to the back of each subject between the scapulae and waist, adjacent to the spinal mid-line. All patch preparations and evaluations were made by trained, experienced technicians under the supervision of the Study Director.

Each day during the duration of the study, patches were removed and the sites were evaluated for irritation using the 6-point scoring system outlined below. After irritation scoring, identical patches were reapplied to the same test sites.

All panelists were instructed to keep the patch test areas as dry as possible while showering or bathing during the course of the study. This procedure was repeated at each visit for a period of fourteen (14) consecutive days, excluding Sundays (Saturday's patches were worn until Monday. Monday's irritation scores were recorded as Sunday's scores and Sunday was counted as an exposure day). Patch test sites were evaluated daily and scores were recorded on a Cumulative Irritation Patch Test recording form. Individual test article scores were calculated via summation of the results for each day. If a dermal reaction of a numerical score of 3 or greater occurred with any of the test articles or adhesive at any point during the study, further patch testing on that subject, at the test site involved was terminated and the attained score was assigned to that site for the subsequent scheduled induction test days.

The Following 6-point Dermal Scoring Scale was Used:
  0=No reaction
  +=Barely-perceptible (minimal, faint, uniform or spotty erythema, numerical value=0.5)
  1=Mild (pink, uniform erythema covering most of the contact site)
  2=Moderate (pink-red erythema visibly uniform in entire contact site)
  Marked (bright-red erythema with/without petechiae or papules)
  4=Severe (deep-red erythema with/without vesiculation or weeping)
Accompanying edema, dryness, hypo-hyperpigmentation or any other observable dermal sequale at any test site will be recorded and described as mild, moderate or severe.

In the event that a subject missed one (1) visit, they were permitted to continue on the study. The following day's score was "carried back" and recorded for the missed visit day. Missing a second visit, at any time, was cause for disqualification and the subject was discontinued from the study.

Results and Discussion

Twenty-two (22/25) subjects satisfactorily completed the test procedure. Three (3/25) test panelists discontinued for personal reasons unrelated to the conduct of the study. Discontinued panelist data are shown up to the point of discontinuation, but are not used in the Results, Discussion or Conclusions sections of this final report.

Cumulative Irritation

Based on twenty-two (22) subjects completing the study, the highest Total cumulative irritation score that could be obtained equals 924 (22 subjects×14 days×"3" [highest obtainable irritation score for any of the test articles]). The highest possible Mean cumulative irritation score that could be obtained equals 42 (924÷22 subjects).

CONCLUSIONS

The fourteen day human cumulative irritation study conducted with eight surfactants, showed that none of the surfactants were as irritating as sodium lauryl sulfate. Test Articles #1 and #2 were the least irritating. Almost a 4-fold greater cumulative irritation response was observed with the test articles (#3–8) when compared to Test Articles #1 and 2. Test Article #4 was associated with the greatest irritation.

Table A summarizes the total cumulative irritancy scores, the mean cumulative irritation scores and ranks the test articles, based on mean cumulative irritancy.

TABLE A

Comparative Cumulative Irritancy Ranking
(Lowest to Highest)

| Test Article Nos. | Total Cum. Irrit. Scores* | Mean Cum. Irrit. Scores** |
|---|---|---|
| #1 | 156.5 | 7.1 |
| #2 | 213.5 | 9.7 |
| #5 | 544 | 24.7 |
| #3 | 544.5 | 24.8 |
| #8 | 547 | 24.9 |
| #6 | 564.5 | 25.7 |
| #7 | 567 | 25.8 |
| #4 | 594.5 | 27.0 |
| #9 | 844.5 | 38.4 |

*Total Cumulative Irritancy Score = (Sum of Total Cumulative Score for 14 days).
**Mean Cumulative Irritation Score = (Total ÷ 22 subjects).

The ranking of test articles by irritancy, from least to most irritating, (based upon the mean cumulative irritancy response) is:

1<2<5<3<8<6<7<4<9

None of the surfactants were found to be as irritating as sodium lauryl sulfate. Almost a 4-fold difference in irritation was observed between the least irritating (Test Article #1) and the most irritating (Test Article #4). Test Article #1 and Test Article #2 showed a similar, minimal, non-cumulative irritation response (7.1 and 9.7) and the other Test Articles (#3, 4, 5, 6, 7, 8) were almost 4-times more irritating (24.7 to 27.0).

Since the mean cumulative irritation for Test Article 3–8 were very similar, the first evaluation day response at which a grade 3 was observed was determined. The first Test Article to be associated with marked (grade 3) erythema was Test Article #3 at the Day 3 observation. The first Test Article associated with sixty-eight percent (68%) of the subject population responding with marked (grade 3) erythema was Test Article #4, at Day 8.

The unobviousness of this invention is illustrated by the following results and observations made during the course of our investigations. In the course of investigation of such combinations for foaming, phase behavior and other performance properties, concurrent investigation of skin irritation properties revealed at least two unexpected results.

Figure 1:
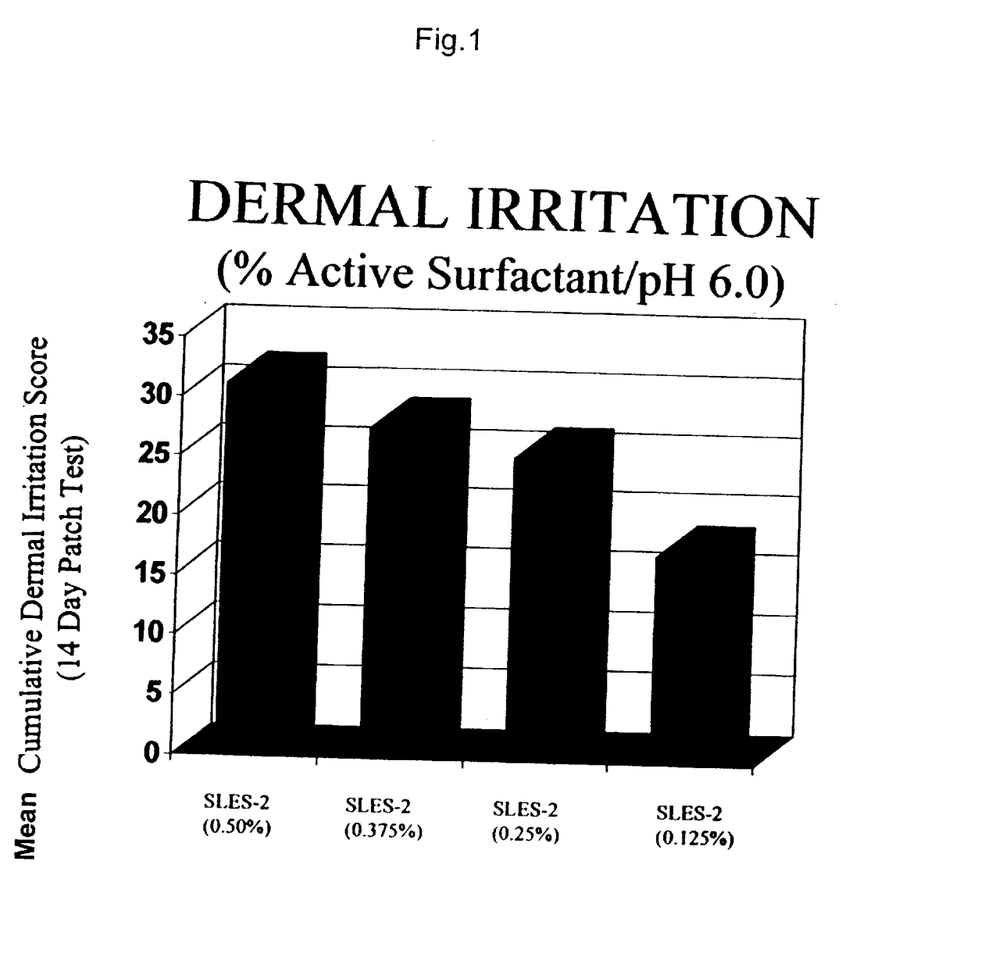
FIG. 1 is a graph of the dermal irritation scores of compositions containing sodium laureth sulfate (SLES-2)

Anionic surfactants such as sodium lauryl sulfate, sodium laureth sulfate (SLES-2) and similar salts of alcohol sulfates, alcohol ether sulfates, and alkyl sulfonates have been widely used as primary surfactants in high foaming personal care products such as hair shampoos, skin and body cleansers, foam baths, etc. While extremely good foaming and cleansing agents, these compounds are generally regarded as strong irritants to the skin and eyes (FIG. 1). To reduce the irritation profiles of these compounds, it is well recognized by knowledgeable formulators that partial substitution of these compounds with other mild surfactants such as sulfosuccinates, sorbitol ester ethoxylates, alkyl monoglyceride alkylates etc., will reduce overall irritation via concentration dilution effect. Other recognized ways to reduce irritation associated with the identified anionic surfactants is through the use of imidazoline derived amphoteric surfactants such as sodium alkylamphoacetates, sodium alkylamphopropionates, etc., and/or alkyl betaines, alkylamidopropyl betaines, alkylamidopropyl hydroxy sultaines, etc. In the art it is generally believed that these compounds form positive synergistic complexes with anionic surfactants resulting in mild systems. These compounds therefore function as true anti-irritation agents as opposed to simple irritation diluents.

Figure 2:
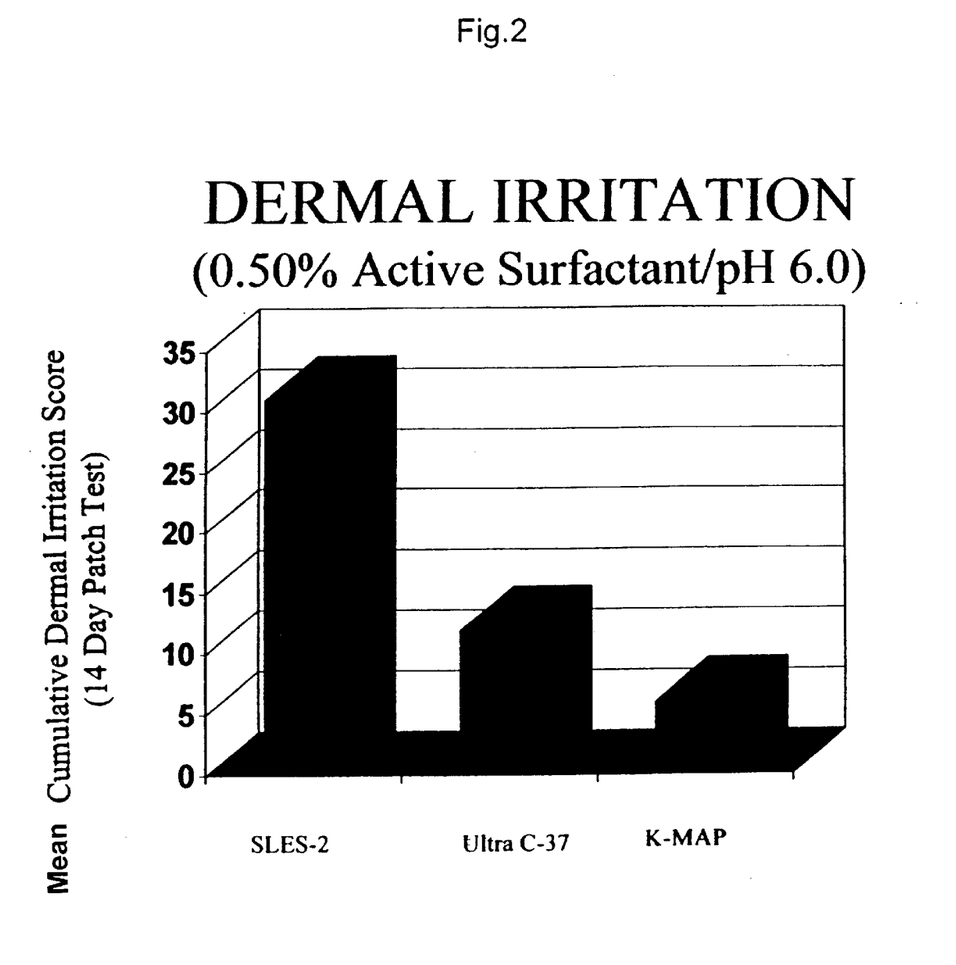
FIG. 2 is a graph of dermal irritation scores of compositions containing SLES-2, or cocoamidoalkylamino monoacetate (Miranol Ultra C-37) or potassium lauryl phosphate (K-MAP)

As anionic surfactants, the various salt forms (sodium, potassium, amine, etc.) of monoalkyl and monoalkyl ether phosphate esters are inherently mild to the skin and eyes as individual surfactants (FIG. 2). Based on traditional thinking, therefore, it would be expected that these compounds when combined with other irritating anionic surfactants such as sodium lauryl sulfate, sodium laureth sulfate, etc., should function as irritation diluents thus reducing the overall system irritation proportional to their use concentration ratios. In addition, it would be expected that these compounds would act in a similar manner as other common anionic surfactants and react synergistically with recognized irritation mollifying agents such as imidazoline derived amphoterics, alkyl betaines, alkylamidopropyl betaine, etc., to reduce the overall system irritation.

Figure 3:
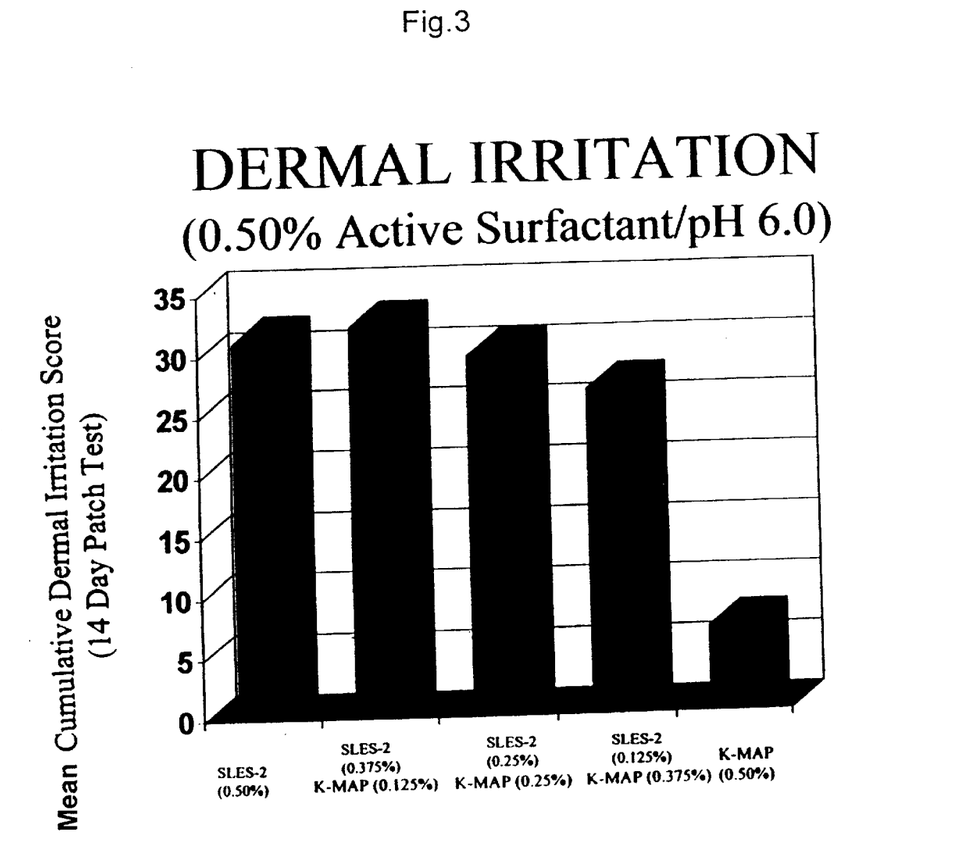
FIG. 3 is a graph of dermal irritation scores of compositions containing SLES-2, or K-MAP or combinations of SLES-2 and K-MAP.
Figure 4:
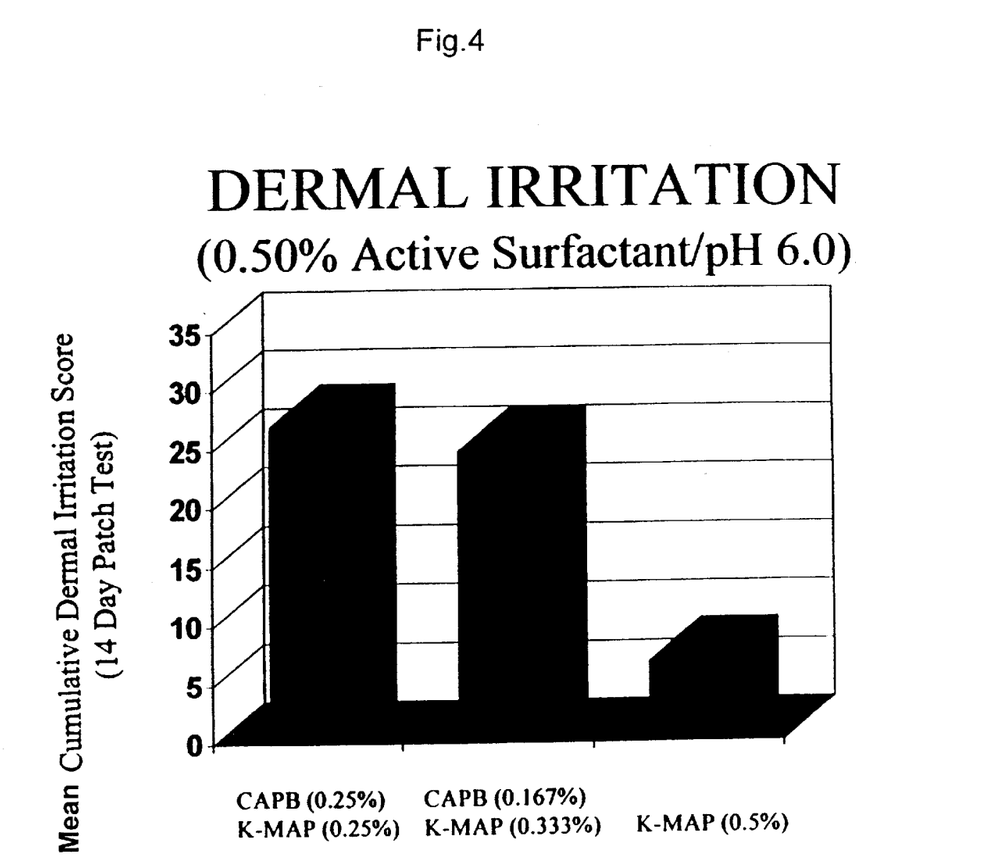
FIG. 4 is a graph of dermal irritation scores for compositions containing K-MAP or combinations of K-MAP and cocoamidopropyl betaine (CAPB)

Surprisingly, when the identified monoalkyl phosphate, potassium lauryl phosphate (K-MAP) was combined with a common anionic surfactant, Sodium Laureth Sulfate (ES-2), the resulting skin irritation profile remained extremely high (FIG. 3). In essence, no irritation dilution effect was observed. Similarly, when the identified monoalkyl phosphate (K-MAP) was combined with cocamidopropyl betaine (CAPB), a recognized irritation mollifying agent, no reduction in irritation was observed (FIG. 4).

Figure 5:
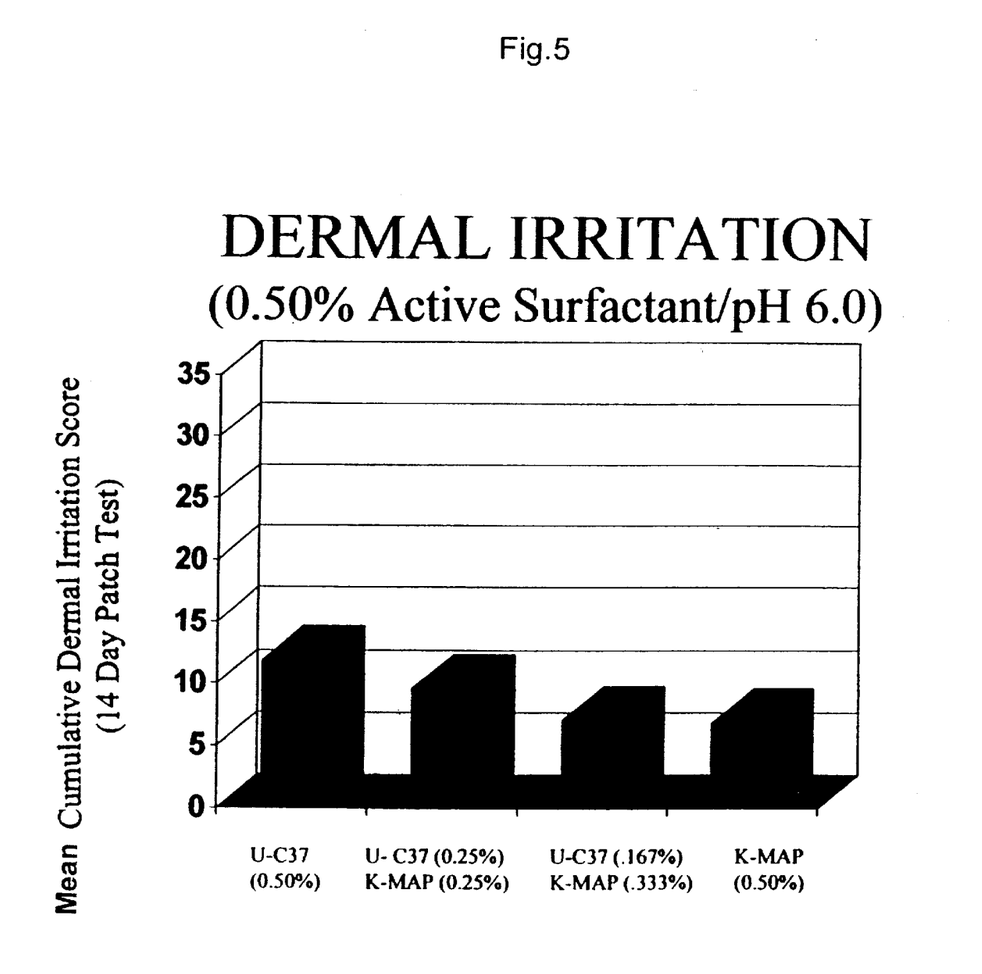
FIG. 5 is a graph of dermal irritation scores of compositions containing Miranol Ultra C-37 or K-MAP or combinations of Miranol C-37 and K-MAP.

Based on these results, it would therefore be expected that the identified monoalkyl phosphate (K-MAP), when combined with imidazoline derived amphoteric surfactants, should also demonstrate negative synergies similar to the monoalkyl phosphate/betaine blend and yield systems that are irritating to the skin. Surprisingly, the combination of these ingredients, K-MAP and sodium cocoamphoacetate (C-37), resulted in systems that were universally mild to the skin (FIG. 5).

It was therefore even more unexpected, and the substance of this invention, when these continuing studies revealed that the blends of phosphate esters with imidazoline based amphoteric surfactants were truly unique in that they displayed positive synergistic effects. This clearly distinguished this combination with phosphate esters above all the other commonly used personal care ionic surfactants and cleansers and these blends produced formulations with high levels of cleaning and foaming, excellent skin after-feel and outstanding mildness. This finding further is unusual and unobvious to one skilled in the art because the art teaches that the various "amphoteric" components, wherein zwitterionic betaine and true amphoteric surfactants (whose net charge can be varied from cationic through zwitterionic to anionic as a function of pH), are used interchangeably in combination with phosphate esters with the same effects, much like with any other anionic surfactant. Our research clearly demonstrates that the phosphate esters are unique among the class of anionic surfactants and especially that the combination with true amphoteric surfactants is unique and distinguished by its superior performance and most importantly, extreme mildness and continuing moisturizing quality above that attainable by combinations with the other, supposedly equivalent, amphoteric/betaines.

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. An aqueous surfactant composition comprising a surfactant consisting essentially of a) a mixture of mono- and di-alkyl phosphate ester salts, with the molar ratio of mono- to di-alkyl phosphate ester being greater than 50:50 and b) an imidazoline based amphoteric surfactant wherein said composition is essentially free of compounds having a tetra-alkyl ammonium moiety.

2. An aqueous surfactant composition of claim 1, wherein the molar ratio of mono- to di-alkyl ester is equal to or greater than 80:20.

3. An aqueous surfactant composition of claim 1, wherein the molar ratio of mono- to di-alkyl ester is equal to or greater than 90:10.

4. An aqueous surfactant composition of claim 1, wherein the salts are selected from the group consisting of sodium, potassium, lithium, ammonium and amine salts.

5. An aqueous surfactant composition of claim 4, wherein alkyl phosphate ester salts comprise about 99% by weight salts of alkyl phosphate esters of $C_{12}$ alcohol.

6. An aqueous surfactant composition of claim 1 having a total solids content of from about 5% to about 40%.

7. An aqueous surfactant composition of claim 6 wherein the ratio of phosphate ester salt surfactants to amphoteric surfactant is from about 10:1 to about 1:10.

8. An aqueous surfactant composition of claim 6 wherein the ratio of phosphate ester salt surfactants to amphoteric surfactant is from about 3:1 to about 1:3.

9. A composition of claim 1 wherein said mixture of mono- and di-alkyl phosphate ester salts is a mixture of compounds having the formula (1) and (2):

wherein $R_1$ and $R_2$ are individually $C_8$–$C_{22}$ linear or branched saturated or unsaturated hydrocarbons, m and n are individually integers from 2 to 4, w, x, y and z are individually integers from 0 to 20 and M is individually hydrogen, an alkali metal, amine or alkanolamine.

10. An aqueous surfactant composition of claim 9, wherein the alkyl phosphate ester salts comprise at least 80% by weight salts of alkyl phosphate esters of predominately $C_8$ to $C_{16}$ linear or branched aliphatic alcohols.

11. An aqueous surfactant composition of claim 10, wherein the aliphatic alcohol comprises predominately $C_{10}$ to $C_{12}$ linear or branched aliphatic alcohols.

12. An aqueous surfactant composition of claim 10, wherein the salts are selected from the group consisting of sodium, potassium, lithium, ammonium and amine salts.

13. An aqueous surfactant composition comprising a surfactant consisting essentially of a) a mixture of mono- and di-alkyl phosphate ester salts, with the molar ratio of mono- to di-alkyl phosphate ester being greater than 50:50 and b) an imidazoline based amphoteric surfactant wherein said composition is essentially free of compounds having a tetra-alkyl ammonium moiety, wherein the amphoteric surfactant is selected from the group consisting of cocoamidoalkylamino monoacetate, cocoamidoalkylamino monopropionate, sodium cocoamidoalkylamino hydroxypropyl sulfonate, and sodium caprylamidoalkylamino hydroxypropyl sulfonate; and wherein said mixture of mono- and di-alkyl phosphate ester salts is a mixture of compounds having the formula (1) and (2):

wherein $R_1$ and $R_2$ are individually $C_8$–$C_{22}$ linear or branched, saturated or unsaturated hydrocarbons, m and n are individually integers from 2 to 4, w, x, y and z are individually integers from 0 to 20 and M is individually hydrogen, an alkali metal, amine or alkanolamine.

14. An aqueous surfactant composition of claim 13, wherein the amphoteric surfactant is cocoamidoalkylamino monoacetate.

15. An aqueous surfactant composition comprising a surfactant consisting essentially of a) a mixture of mono- and di-alkyl phosphate ester salts, with the molar ratio of mono- to di-alkyl phosphate ester being greater than 50:50 and b) an imidazoline based amphoteric surfactant wherein said composition is essentially free of compounds having a tetra-alkyl ammonium moiety and wherein the amphoteric surfactant is selected from the group consisting of cocoamidoalkylamino monoacetate, cocoamidoalkylamino monopropionate, sodium cocoamidoalkylamino hydroxypropyl sulfonate, and sodium caprylamidoalkylamino hydroxypropyl sulfonate.

* * * * *